United States Patent [19]

Poppendiek et al.

[11] Patent Number: 4,534,663
[45] Date of Patent: Aug. 13, 1985

[54] MEANS AND TECHNIQUES FOR TESTING OF HEAT INSULATION MATERIALS

[75] Inventors: Heinz F. Poppendiek, La Jolla; Cullen M. Sabin, Solana Beach, both of Calif.

[73] Assignee: Geoscience Ltd, Solana Beach, Calif.

[21] Appl. No.: 539,665

[22] Filed: Oct. 6, 1983

[51] Int. Cl.[3] ............................................. G01N 25/18
[52] U.S. Cl. ........................................ 374/43; 374/30; 374/11
[58] Field of Search ...................... 374/30, 29, 43, 44, 374/10

[56] References Cited

U.S. PATENT DOCUMENTS

| | | | |
|---|---|---|---|
| 2,272,245 | 2/1942 | Kuck | 374/44 X |
| 2,296,815 | 9/1942 | Evans | 374/43 X |
| 3,987,660 | 10/1976 | Pelanne | 374/44 X |
| 4,095,454 | 6/1978 | Fisher | 374/43 |
| 4,198,859 | 4/1980 | Holtermann | 374/30 |
| 4,246,785 | 1/1981 | Sellers et al. | 374/159 X |

OTHER PUBLICATIONS

"Evaluation Methods", V. F. Zinchenko et al., pp. 108–112 of Institute of Polymer Materials (Latvian SSC, RICA), Polym. Mech. (U.S.A., vol. 12, No. 1, publ. 1/1977.

Primary Examiner—Daniel M. Yasich
Attorney, Agent, or Firm—Frank E. Mauritz

[57] ABSTRACT

The quality of heat insulation materials is tested and/or compared in a portable structure in which two heat insulation materials are subjected simultaneously to heat flow from a single common metal-clad heating element and the quantity of heat flow through said material is measured and compared. In one case the portable structure has two conveniently accessible cavities within which equal amounts of such insulation, in flat form, may be placed in contact with corresponding opposite sides of a single common metal-clad planar heat source. In a modification of the invention two tubular insulating materials each of the form and type for insulating pipe, is placed around a metal-clad round heating element and the amount of heat flowing from the heating element and through a corresponding one of said materials is measured and compared using individual thermopiles secured to the outer surface of each material.

4 Claims, 4 Drawing Figures

U.S. Patent    Aug. 13, 1985    4,534,663

MEANS AND TECHNIQUES FOR TESTING OF HEAT INSULATION MATERIALS

The present invention relates to improved means and techniques for measuring and/or comparing the quality of different heat insulation materials.

An object of the present invention is to provide simple, inexpensive and portable apparatus for readily and accurately establishing the relative merits of different insulating materials.

Figure 1:
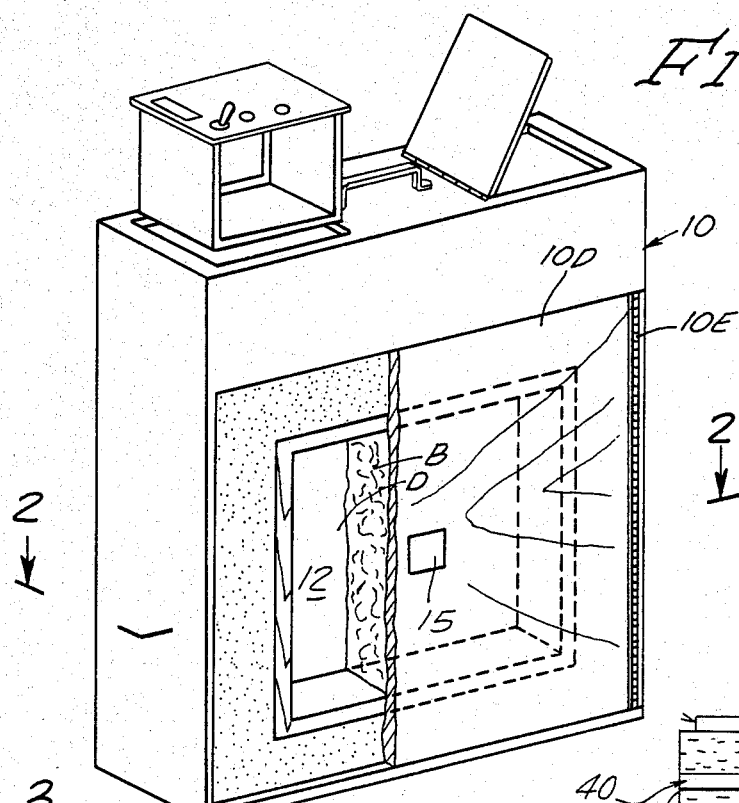
Figure 4:
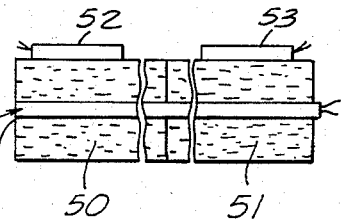
Figure 3:
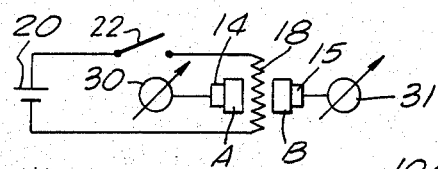

Another object of the present invention is to provide new and improved apparatus for comparing insulation materials featured by the fact that the materials under comparison are subjected to a common single heat source in the same manner and the quantity of heat flowing through the individual materials is measured or indicated for purposes of establishing their merit as heat insulation means. In the drawings, FIG. 1 is a perspective view of apparatus embodying features of the present invention with some parts broken away for purposes of illustrating internal structure, FIG. 2 is a sectional view taken substantially as indicated by the line 2—2 in FIG. 1, FIG. 3 is a simplified wiring diagram of the electrical circuitry, and FIG. 4 illustrates a modification of the invention.

Figure 2:
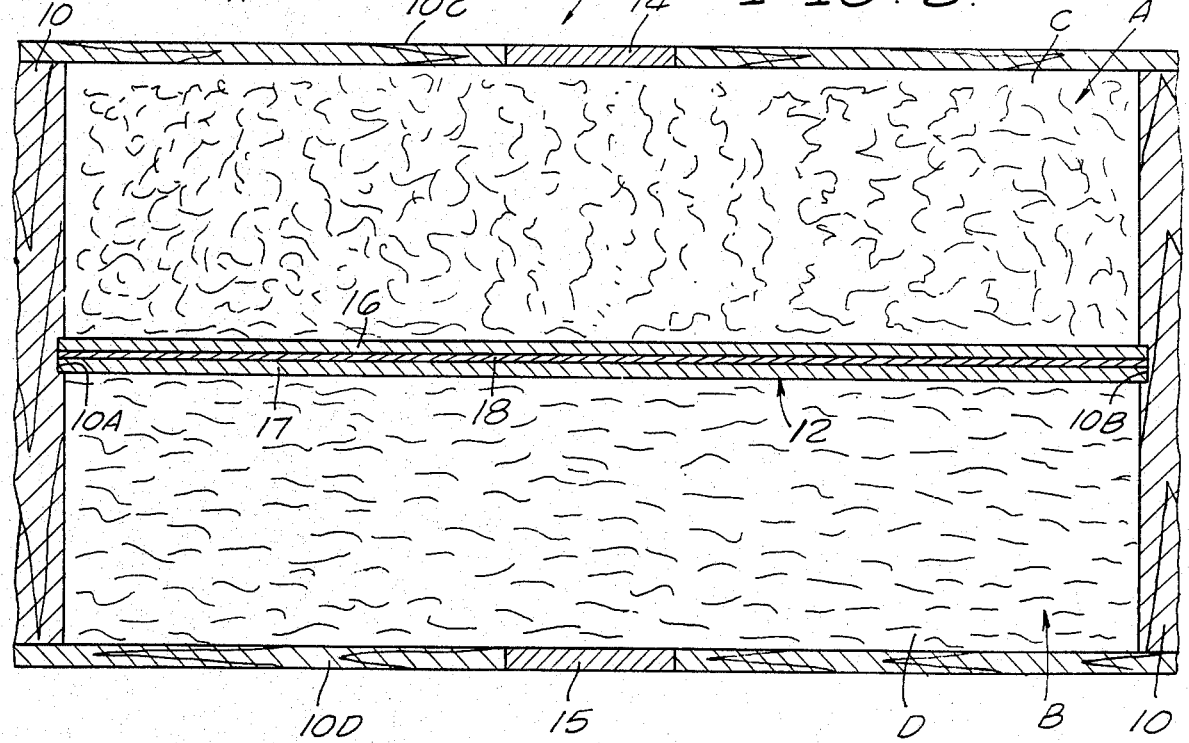

As illustrated in FIG. 2 the testing apparatus includes a housing structure 10 for confining two different insulating materials A and B in corresponding rectangular cavities C and D of equal size and volume on opposite sides of a special flat heat source 12, the source 12 being secured to the structure 10 as, for example, by recessing at 10A and 10B.

Access to the cavities C and D for purposes of inserting and removing corresponding insulation materials A and B is achieved by moving cover members 10C and 10D respectively which for that purpose are each pivoted or hinged on the structure 10, as, for example, by piano type hinges. The hinge for cover member 10D is illustrated at 10E in FIG. 1 and a like hinge (not shown) mounts the other cover member 10C on structure 10 which is generally of wood.

The cover members 10C and 10D have secured thereto a corresponding centrally disposed heat flux measuring means 14, 15 for measuring the quantity of heat flowing from the heat source 12 through corresponding heat insulation materials A, B.

The heat source 12 comprises a pair of thick aluminum sheets 16, 17 between which is conductively sandwiched a flat electrical heating element 18 to which electrical heating energy is supplied from a voltage source 20, FIG. 3, through switch 22.

The thick aluminum plates 16, 17 serve to produce a uniform and constant temperature heat source.

Should, under these conditions, the material A be inferior to material B as to insulating quality, a larger amount of heat flows through insulating material A than through material B and this condition is ascertainable by comparing the readings on meters 30, 31.

Preferably the area of the plates 16, 17 is greater than the area of corresponding heat flux measuring means 14, 15 so that the heat flux lines representing heat flow between the plates and the measuring means are representable by parallel heat flow lines with minimum or substantially no flaring or fringing of heat flow occurring in the insulating material.

Each of the cavities may have a crosssection of 14½ by 14½ inches comparable to dimensions of cavities in uninsulated building constructions.

The switch 22 in FIG. 3 may be operated and controlled (by means not shown) so as to maintain a constant temperature at any particular point or region in the heated system.

In the modification shown in FIG. 4 for testing of round insulation used in insulating pipes, there is again a metal-clad heating element 40 but in this case the heating element is in the form of a cylinder over which different tubular pipe insulating materials 50, 51 of equal size may be snugly placed. The outer part of the heating element is in the form of a high conductivity material such as a copper tube 62 and it is internally heated in such a manner that its temperature is maintained uniform over its length.

Materials 50, 51 have corresponding equal size thermopiles 52, 53 secured thereto as, for example, by adhesive tape or a clamp (not shown) to cover only a portion of the outer surface of corresponding insulation 50, 51 so as to measure the amount of heat flowing from heater 40 to each of the thermopiles. Likewise as taught herein, the heat flux measuring means 14, 15 in FIG. 1 may for example be thermopiles. A second measurement may be made after reversing the positions of insulation in either the arrangement in FIG. 1 or in FIG. 4.

We claim:

1. Insulation testing apparatus comprising, a single heat source; said heat source being a single elongated electrical heating element; said heat source being metal-clad along its length by a high heat conductivity metal material which is in good heat conducting relationship to said heating element and which is internally heated by said element such that the temperature of said metal material is substantially uniform along its length; metal material which is heated by said elongated electrical element with said two insulating materials each having an inner surface and an outer surface and with said inner surface of each insulating material being in direct contact with said metal material without any air space therebetween; means for measuring the difference in the quantity of heat conducted through said different insulating materials; said measuring means including a first thermopile means and a second thermopile means mounted on wall means in said apparatus and in thermal contact respectively with a corresponding outer surface of said two insulating materials without any air space therebetween such that heat flows solely by conduction and without radiation or convection from the heated metal-clad heat source through each of said two insulating materials to a corresponding one of said thermopile means, said first thermopile means measuring the amount of heat passing through one of said materials; and said second thermopile means measuring the amount of heat flowing through the other one of said insulating materials.

2. Apparatus as set forth in claim 1 in which said heat source is a flat electrical heating element sandwiched between two metal plates which are heated by said heating element with one of said plates being in contact with one of said insulating materials, and the other one of said plates being in contact with the other one of said insulating materials.

3. Apparatus as set forth in claim 1 in which said heat source is a metal-clad cylindrical heater upon which said different insulation materials may be snugly fitted during operation of said measuring means.

4. Apparatus as set forth in claim 1 in which the outer surface area of the insulating material contacted by the corresponding thermopile means is substantially less that each inner surface area contacted by said metal-clad heat source so that heat flow through the insulating materials is in generally parallel lines without substantially no flaring or fringing of heat flow in the insulating materials.

* * * * *